US011478146B2

United States Patent
Yamanari

(10) Patent No.: US 11,478,146 B2
(45) Date of Patent: Oct. 25, 2022

(54) OPTICAL COHERENCE TOMOGRAPHIC DEVICE

(71) Applicant: Tomey Corporation, Nagoya (JP)

(72) Inventor: Masahiro Yamanari, Nagoya (JP)

(73) Assignee: TOMEY CORPORATION, Nagoya (JP)

( * ) Notice: Subject to any disclaimer, the term of this patent is extended or adjusted under 35 U.S.C. 154(b) by 953 days.

(21) Appl. No.: 16/250,376

(22) Filed: Jan. 17, 2019

(65) Prior Publication Data

US 2019/0223717 A1     Jul. 25, 2019

(30) Foreign Application Priority Data

Jan. 22, 2018  (JP) .............................. JP2018-008265

(51) Int. Cl.
*G01B 9/02* (2022.01)
*A61B 3/12* (2006.01)
(Continued)

(52) U.S. Cl.
CPC ............ *A61B 3/1233* (2013.01); *A61B 3/102* (2013.01); *G01B 9/02091* (2013.01)

(58) Field of Classification Search
CPC ..... A61B 3/1233; A61B 3/1241; A61B 3/102; G01B 9/02091
See application file for complete search history.

(56) References Cited

U.S. PATENT DOCUMENTS 10,010,247 B2 *   7/2018  Fleming ................... A61B 3/14
2014/0334707 A1  11/2014  Teiwes et al.
(Continued)

FOREIGN PATENT DOCUMENTS

EP      3278720 A1    2/2018
JP    2014-527434 A  10/2014
(Continued)

OTHER PUBLICATIONS

D. A. Boas and A. G. Yodh, "Spatially varying dynamical properties of turbid media probed with diffusing temporal light correlation," J. Opt. Soc. Am. A 14, 192-215 (1997) (Year: 1997).*
(Continued)

*Primary Examiner* — Dominic J Bologna
*Assistant Examiner* — Jonathon Cook
(74) *Attorney, Agent, or Firm* — Shumaker, Loop & Kendrick, LLP

(57) ABSTRACT

An optical coherence tomographic device may include: a light source; a measurement light generator that generates measurement light and generates reflected light from a target region in a scattering sample by irradiating the target region with the measurement light; a reference light generator that generates reference light; an interference light generator that generates interference light by combining the reflected light and the reference light; an interference light detector that detects the interference light and generates interference signals by converting the interference light; and a processor. The processor may cause the OCT device to execute: acquiring tomographic images for a same cross section in the target region in time series from the interference signals; calculating an entropy of the generated interference signals based on the tomographic images; and specifying a dynamic part in the tomographic images based on the calculated entropy.

7 Claims, 8 Drawing Sheets

(51) Int. Cl.
 *G01B 9/02091* (2022.01)
 *A61B 3/10* (2006.01)

(56) References Cited

U.S. PATENT DOCUMENTS

| | | | |
|---|---|---|---|
| 2016/0066798 A1 | 3/2016 | Wang et al. | |
| 2017/0055830 A1* | 3/2017 | Kotoku | A61B 3/0058 |
| 2017/0065170 A1* | 3/2017 | Yamashita | A61B 3/102 |
| 2017/0209037 A1* | 7/2017 | Sumiya | A61B 3/0058 |
| 2017/0221217 A1 | 8/2017 | Hong et al. | |
| 2018/0153396 A1* | 6/2018 | Uchida | A61B 3/102 |
| 2018/0344149 A1* | 12/2018 | Chong | A61B 3/0025 |

FOREIGN PATENT DOCUMENTS

| | | |
|---|---|---|
| WO | 2013022986 A1 | 2/2013 |
| WO | 2014085911 A1 | 6/2014 |

OTHER PUBLICATIONS

T. Chanwimaluang and Guoliang Fan, "An efficient blood vessel detection algorithm for retinal images using local entropy thresholding," 2003 IEEE International Symposium on Circuits and Systems (ISCAS), 2003, pp. V-V, doi: 10.1109/ISCAS.2003.1206162. (Year: 2003).*

Yousefi et al., "Super-resolution spectral estimation of optical micro-angiography for quantifying blood flow within microcirculatory tissue beds in vivo", Biomedical Optics Express, Jul. 1, 2013, vol. 4, No. 7, p. 1214-1228.

Makita et al., "Noise-immune complex correlation for optical coherence angiography based on standard and Jones matrix optical coherence tomography", Biomedical Optics Express, Apr. 1, 2016, vol. 7, No. 4, p. 1525-1548.

* cited by examiner

ABSTRACT
OPTICAL COHERENCE TOMOGRAPHIC DEVICE

CROSS-REFERENCE

This application claims priority to Japanese Patent Application No. 2018-008265, filed on Jan. 22, 2018, the entire contents of which are incorporated herein by reference.

TECHNICAL FIELD

The technique disclosed herein relates to an optical coherence tomographic device.

BACKGROUND ART

Techniques for specifying a dynamic part in a scattering sample (such as a position of a blood vessel in a living organism) are in development. For example, fluorescence imaging that is employed in a wide variety of clinical uses nowadays is known as a method for specifying a dynamic part in a scattering sample. In the fluorescence imaging, a dynamic part in a scattering sample is specified by injecting a contrast medium containing fluorochrome into a patient's body and detecting fluorescence exhibited by the fluorochrome. Further, as another method for specifying a dynamic part in a scattering sample, a method that uses an optical coherence tomography (OCT) is known. By using the OCT, a dynamic part in a scattering sample can be specified noninvasively. For example, US Patent Application Publication No. 2016/0066798 describes an example of a method of blood vessel imaging in a scattering sample by using OCT.

SUMMARY

In the aforementioned fluorescence imaging, the contrast medium needs to be injected into the patient's body, and thus there was a problem that patient's affliction is grave. Further, in a method using OCT as described in US Patent Application Publication No. 2016/0066798, there was a problem that the dynamic part in the scattering sample cannot be specified with high accuracy. The disclosure herein discloses a technique that detects a dynamic part in a scattering sample noninvasively and with high accuracy.

An optical coherence tomographic device disclosed herein may comprise: a light source; a measurement light generator configured to generate measurement light by using light from the light source and to generate reflected light from a target region in a scattering sample by irradiating the target region with the measurement light; a reference light generator configured to generate reference light by using the light from the light source; an interference light generator configured to generate interference light by combining the reflected light from the target region generated in the measurement light generator and the reference light generated in the reference light generator; an interference light detector configured to detect the interference light generated in the interference light generator and to generate interference signals by converting the interference light; a processor; and a memory storing computer-readable instructions therein, the computer-readable instructions, when executed by the processor, causing the optical coherence tomographic device to execute: acquiring a plurality of tomographic images for a same cross section in the target region in time series from the interference signals generated in the interference light detector; calculating an entropy of the generated interference signals based on the plurality of tomographic images acquired in time series; and specifying a dynamic part in the tomographic images based on the calculated entropy of the generated interference signals.

In the optical coherence tomographic device as above, the plurality of tomographic images (interference signals) is acquired for the same cross section in the specific target region in time series. by which the entropy of the acquired interference signals can be calculated. Tomographic images hardly change over time at a stationary part in the scattering sample, whereas the tomographic images change over time at a dynamic part in the scattering sample. Due to this, from a time-series perspective, the entropy is low at the stationary part such as a tissue that hardly moves in the scattering sample, and it is high at the dynamic part such as a blood vessel. Due to this, the dynamic part can be specified noninvasively and with high accuracy by calculating the entropy of the interference signals.

DETAILED DESCRIPTION

Figure 1:
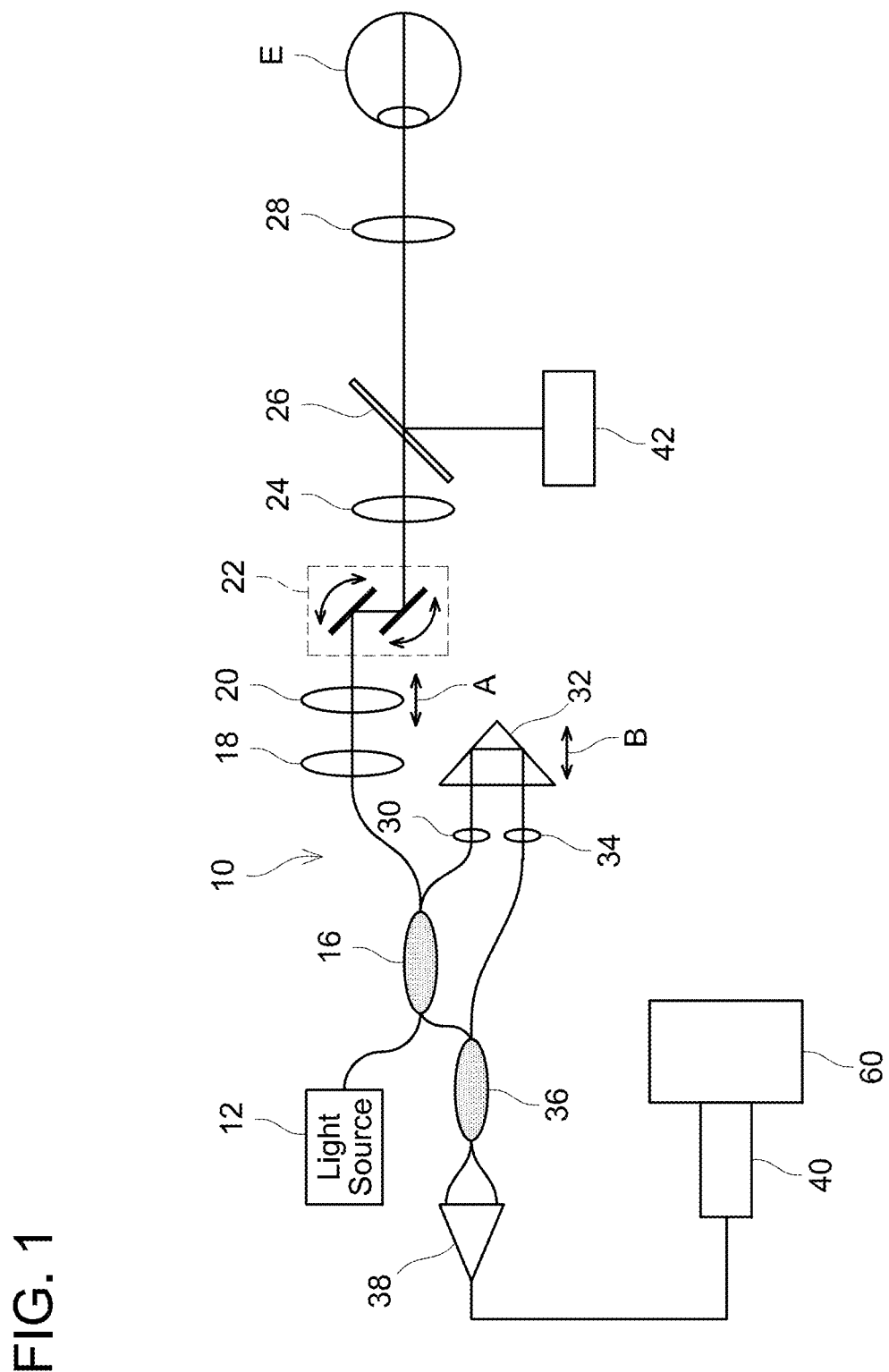
FIG. 1 shows a schematic configuration of an optical system of an optical coherence tomographic device according to an embodiment.

Representative, non-limiting examples of the present invention will now be described in further detail with reference to the attached drawings. This detailed description is merely intended to teach a person of skill in the art further details for practicing preferred aspects of the present teachings and is not intended to limit the scope of the invention. Furthermore, each of the additional features and teachings disclosed below may be utilized separately or in conjunction with other features and teachings to provide improved optical coherence tomographic devices, as well as methods for using and manufacturing the same.

Moreover, combinations of features and steps disclosed in the following detailed description may not be necessary to practice the invention in the broadest sense, and are instead taught merely to particularly describe representative examples of the invention. Furthermore, various features of the above-described and below-described representative examples, as well as the various independent and dependent claims, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

Some of the features characteristic to below-described embodiment will herein be listed. It should be noted that the respective technical elements are independent of one another, and are useful solely or in combinations. The combinations thereof are not limited to those described in the claims as originally filed.

(Feature 1) In the optical coherence tomographic device disclosed herein, the computer-readable instructions, when executed by the processor, may further cause the optical coherence tomographic device to execute: calculating an entropy of noise component in the generated interference signals based on the plurality of tomographic images acquired in time series; and correcting the entropy of the generated interference signals by subtracting the entropy of noise component from the entropy of the generated interference signals. The entropy of the generated interference signals includes the entropy of the noise component. Here, randomness (entropy) which authentic interference signals possess is statistically not correlated with randomness (entropy) caused by the noise component. Due to this, the entropy of the generated interference signals is a sum of the entropy which the authentic interference signals possess and the entropy of the noise component. Therefore, the entropy of the authentic interference signals can be calculated by calculating the entropy of the noise component and subtracting this from the entropy of the generated interference signals. By doing so, the entropy of the interference signals can accurately be calculated, and a dynamic part can more accurately be specified.

(Feature 2) In the optical coherence tomographic device disclosed herein, the computer-readable instructions, when executed by the processor, may further cause the optical coherence tomographic device to execute: acquiring a plurality of tomographic images for each of a plurality of cross sections in the target region in time series; and generating specified tomographic images respectively for the plurality of cross sections by executing the calculating of the entropy of the generated interference signals and the specifying of the dynamic part to each of the plurality of cross sections, each of the specified tomographic images specifying the dynamic part in corresponding one of the plurality of cross sections. According to such a configuration, the target region can be grasped three-dimensionally. Due to this, an examiner can more accurately grasp the dynamic part of the target region.

(Feature 3) In the optical coherence tomographic device disclosed herein, the computer-readable instructions, when executed by the processor, may further cause the optical coherence tomographic device to execute: generating a front image of the target region by using three-dimensional image data obtained by superimposing the specified tomographic images. According to such a configuration, a two-dimensional front image is generated for the target region for which the dynamic part has been specified. Due to this, the examiner can more easily grasp the dynamic part in the target region.

(Feature 4) In the optical coherence tomographic device disclosed herein, the target region may comprise a blood vessel. The dynamic part may be the blood vessel. Since the blood vessel moves over time by blood flow, it can be regarded as the dynamic part. Due to this, a position of the blood vessel can be specified noninvasively by using the tomographic images.

EMBODIMENT

Hereinbelow, an optical coherence tomographic device according to an embodiment will be described. As shown in FIG. 1, the optical coherence tomographic device includes an interference optical system 10 configured to cause reflected light reflected from a subject eye E and reference light to interfere with each other, an observation optical system 42 configured to observe an anterior part of the subject eye E, an alignment optical system (not shown) configured to align the optical coherence tomographic device in a predetermined positional relationship with the subject eye E, and a K-clock generator 56 (shown in FIG. 2) configured to generate K-clock signals. Since a configuration in a known ophthalmology device may be used as the alignment optical system, a detailed description thereof will be omitted.

The interference optical system 10 includes a light source 12, a measurement optical system configured to irradiate inside of the subject eye E with light from the light source 12 and generate reflected light therefrom, a reference optical system configured to generate reference light from the light of the light source 12, and a balance detector 38 configured to detect interference light that is a combination of the reflected light guided by the measurement optical system and the reference light guided by the reference optical system.

The light source 12 is a wavelength-sweeping light source, and is configured to change a waveform of the light emitted therefrom at a predetermined cycle. When the wavelength of the light emitted from the light source 12 changes, a reflected position of reflected light that interferes with the reference light, among reflected light from respective parts of the subject eye E in a depth direction, changes in the depth direction of the subject eye E in accordance with the wavelength of the emitted light. Due to this, it is possible to specify positions of the respective parts (such as a crystalline lens and a retina) inside the subject eye E by measuring the interference light while changing the wavelength of the emitted light.

The measurement optical system includes fiber couplers 16, 36, a collimator lens 18, a focus lens 20, a Galvano mirror 22, a lens 24, a dichroic mirror 26, and an object lens 28. Light outputted from the light source 12 is inputted to the fiber coupler 16 through an optical fiber. The light inputted to the fiber coupler 16 is split into measurement light and reference light in the fiber coupler 16 and they are outputted therefrom. The measurement light outputted from the fiber coupler 16 is inputted to the collimator lens 18 through an optical fiber. The measurement light outputted to the collimator lens 18 enters the subject eye E through the focus lens 20, the Galvano mirror 22, the lens 24, the dichroic mirror 26, and the object lens 28. Reflected light from the subject eye E is inputted to the collimator lens 18 through the object lens 28, the dichroic mirror 26, the lens 24, the Galvano mirror 22, and the focus lens 20, in an opposite direction from the above. The reflected light inputted to the collimator lens 18 is inputted to the fiber coupler 16 through the optical fiber. The reflected light inputted to the fiber coupler 16 is inputted to one of inputs of the fiber coupler 36 through an optical fiber.

Further, the measurement optical system includes a second driver 48 (shown in FIG. 2) configured to move the focus lens 20 forward and backward in an optical axis direction, and a third driver 50 (shown in FIG. 2) configured to tilt the Galvano mirror 22 with respect to an optical axis. A position of a focal point of the light entering the subject eye E changes in the depth direction of the subject eye E by the second driver 48 moving the focus lens 20 in a direction of an arrow A in FIG. 1. Further, an irradiation position of the measurement light to the subject eye E is scanned by the third driver 50 tilting the Galvano mirror 22.

The reference optical system includes the fiber coupler 16, collimator lenses 30, 34, a prism 32, and the fiber coupler 36. The reference light outputted from the fiber coupler 16 is inputted to the collimator lens 30 through an optical fiber. The reference light inputted to the collimator lens 30 is reflected at the prism 32, and then is outputted to the collimator lens 34. The reference light inputted to the collimator lens 34 is inputted to another one of the inputs of the fiber coupler 36 through an optical fiber.

Further, the reference optical system includes a fourth driver 52 (shown in FIG. 2) configured to move the prism 32 forward and backward with respect to the collimator lenses 30, 34. An optical path length of the reference optical system changes by the fourth driver 52 moving the prism 32 in a direction of an arrow B in FIG. 1. Due to this, the optical path length of the reference optical system can be adjusted to substantially match an optical path length of the measurement optical system.

The fiber coupler 36 is configured to combine the reflected light from the subject eye E and the reference light that were inputted thereto to generate interference light. The fiber coupler 36 is further configured to split the generated interference light into two interference light having phases that differ by 180 degrees from each other, and input them to the balance detector 38. The balance detector 38 is configured to execute a process for differential amplification and a process for reducing noise on the two interference light having the phases that differ by 180 degrees, which are inputted from the fiber coupler 36, to convert them into electric signals (interference signals). The balance detector 38 is configured to output the generated interference signals to an AD converter 40. The AD converter 40 is configured to execute A/D conversion on the inputted interference signals, and sample them as digital signals. The sampled interference signals are outputted to a processor 60.

The K-clock generator 56 (shown in FIG. 2) is configured to optically generate sample clock (K-clock) signals from the light of the light source 12 to sample the interference signals at a regular interval frequency (frequency interval that is equalized with respect to light frequency). Further, the generated K-clock signals are outputted toward the processor 60. Due to this, the processor 60 samples the interference signals based on the K-clock signals, by which distortion in the interference signals can be suppressed and deterioration in resolution can be prevented. In the present embodiment, the interference signals that were sampled at timings defined by the K-clock signals are inputted to the processor 60, however, no limitation is placed to this configuration. For example, the processor 60 may execute a process to scale data sampled at a predetermined time interval by using a function indicating a frequency with respect to a preset sweep time, or a sweep profile that is acquired simultaneously therewith.

The observation optical system 42 is configured to irradiate the subject eye E with observation light via the dichroic mirror 26, and captures reflected light reflected from the subject eye E (that is, reflected light of the irradiated observation light). Here, the dichroic mirror 26 allows the light from the light source 12 of the interference optical system 10 pass therethrough, while it reflects the light from a light source of the observation optical system 42. Due to this, in the optical coherence tomographic device according to the present embodiment, the measurement by the interference optical system 10 and the observation of the anterior part by the observation optical system 42 can be carried out simultaneously. Since a configuration used in a known optical coherence tomographic device can be used as the observation optical system 42, a description of its detailed configuration will be omitted. Further, the optical coherence tomographic device according to the present embodiment may be provided with a vision fixation target optical system configured to lead vision fixation of the subject to facilitate the measurement, and may be provided with a SLO optical system configured to acquire a planar image of a fundus of the subject eye E.

Further, the optical coherence tomographic device according to the present embodiment includes a position adjusting mechanism 44 (shown in FIG. 2) configured to adjust a position of the optical coherence tomographic device with respect to the subject eye E, and a first driver 46 (shown in FIG. 2) configured to drive this position adjusting mechanism 44. A process to adjust the position by the position adjusting mechanism 44 will be described later.

Figure 2:
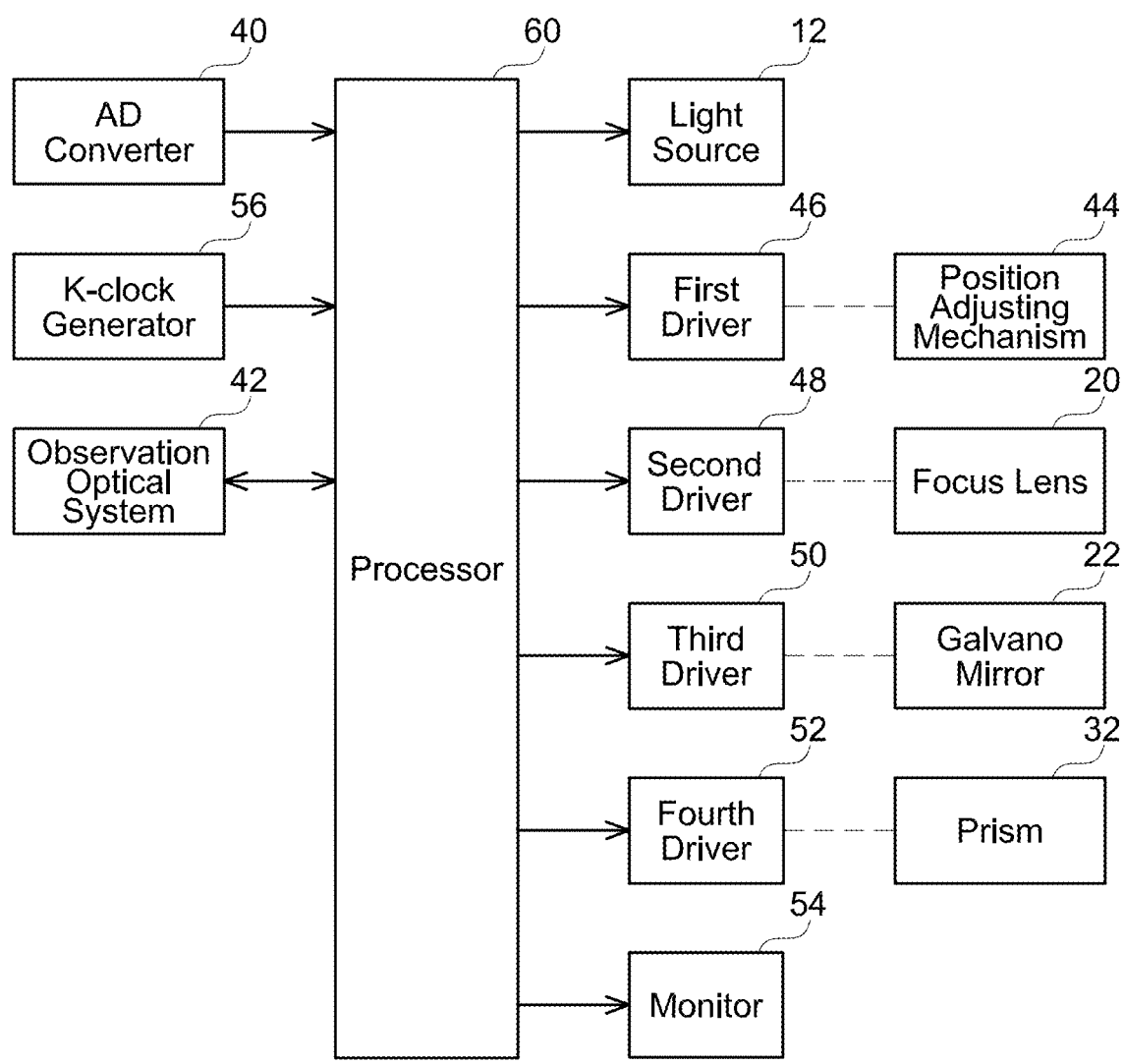
FIG. 2 is a block diagram of a control system of the optical coherence tomographic device according to the embodiment.

Next, a configuration of a control system of the optical coherence tomographic device according to the present embodiment will be described. As shown in FIG. 2, the optical coherence tomographic device is controlled by the processor 60. The processor 60 includes a microcomputer (microprocessor) constituted of CPU, ROM, RAM, and the like. The processor 60 is connected to the light source 12, the first to fourth drivers 46 to 52, a monitor 54, and the observation optical system 42. The processor 60 is configured to control on/off of the light source 12, and drive the respective units 42, 20, 22, 32 by controlling the first to fourth drivers 46 to 52. Further, the processor 60 is configured to control the observation optical system 42 to display an image of the anterior part captured by the observation optical system 42 on the monitor 54. Further, the processor 60 is also connected to the AD converter 40 and the K-clock generator 56. The K-clock signals from the K-clock generator 56 are inputted to the processor 60, and the interference signals sampled at the timings according to the K-clock signals are inputted to the processor 60 from the AD converter 40. The processor 60 executes calculation processes, such as a Fourier transform process, on the interference signals from the AD converter 40 to generate tomographic images. Data inputted to the processor 60 and calculation results thereof are stored in a memory (not shown).

Figure 3:
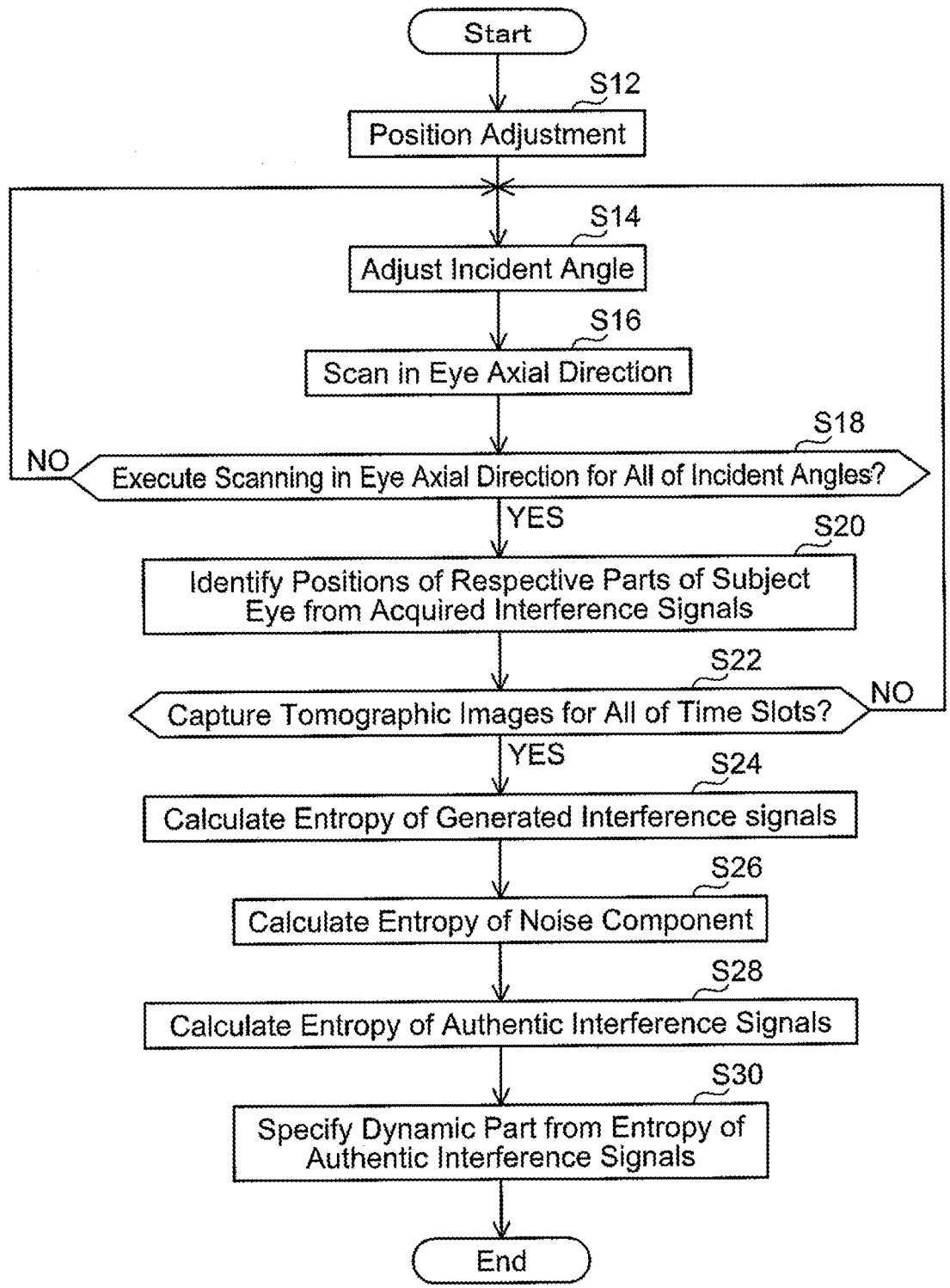
FIG. 3 is a flowchart showing an example of a process to specify a dynamic part in a subject eye by using the optical coherence tomographic device according to the embodiment.

Next, a process to specify a dynamic part of the subject eye E by using the optical coherence tomographic device according to the present embodiment will be described with reference to FIGS. 3 to 7. FIG. 3 is a flowchart showing an example of the process to specify a dynamic part of the subject eye E by using the optical coherence tomographic device according to the present embodiment. In FIG. 3, steps S12 to S22 are processes to capture a plurality of tomographic images for a same cross section of the subject eye E in time series, and steps S24 to S30 are processes to specify a dynamic part in the scattering sample from the acquired tomographic images.

As shown in FIG. 3, firstly, the examiner operates an operation member, such as a joystick which is not shown, to position the optical coherence tomographic device with respect to the subject eye E (S12). That is, the processor 60 drives the position adjusting mechanism 44 by controlling the first driver 46 according to the examiner's operation on the operation member. Due to this, positions of the optical coherence tomographic device with respect to the subject eye E in xy directions (vertical and horizontal directions) and in a z direction (a direction along which the optical coherence tomographic device moves forward/backward with respect to the subject eye E) are adjusted. Further, the processor 60 drives the second driver 48 to adjust a position of the focus lens 20, and drives the fourth driver 52 to adjust a position of the prism 32. Due to this, the position of the focal point of the light entering the subject eye E from the light source 12 is set to a predetermined position in the subject eye E (such as an anterior surface of the cornea), and a zero-point position where the optical path length of the measurement optical system matches the optical path length of the reference optical system is set to a predetermined position on the subject eye E (such as the anterior surface of the cornea).

Next, the processor 60 drives the third driver 50 to adjust the Galvano mirror 22 to one of scan angles within a scan angle range (S14). Due to this, the light from the light source 12 is to enter the subject eye E at an incident position and at an incident angle corresponding to the adjusted scan angle.

Figure 4:
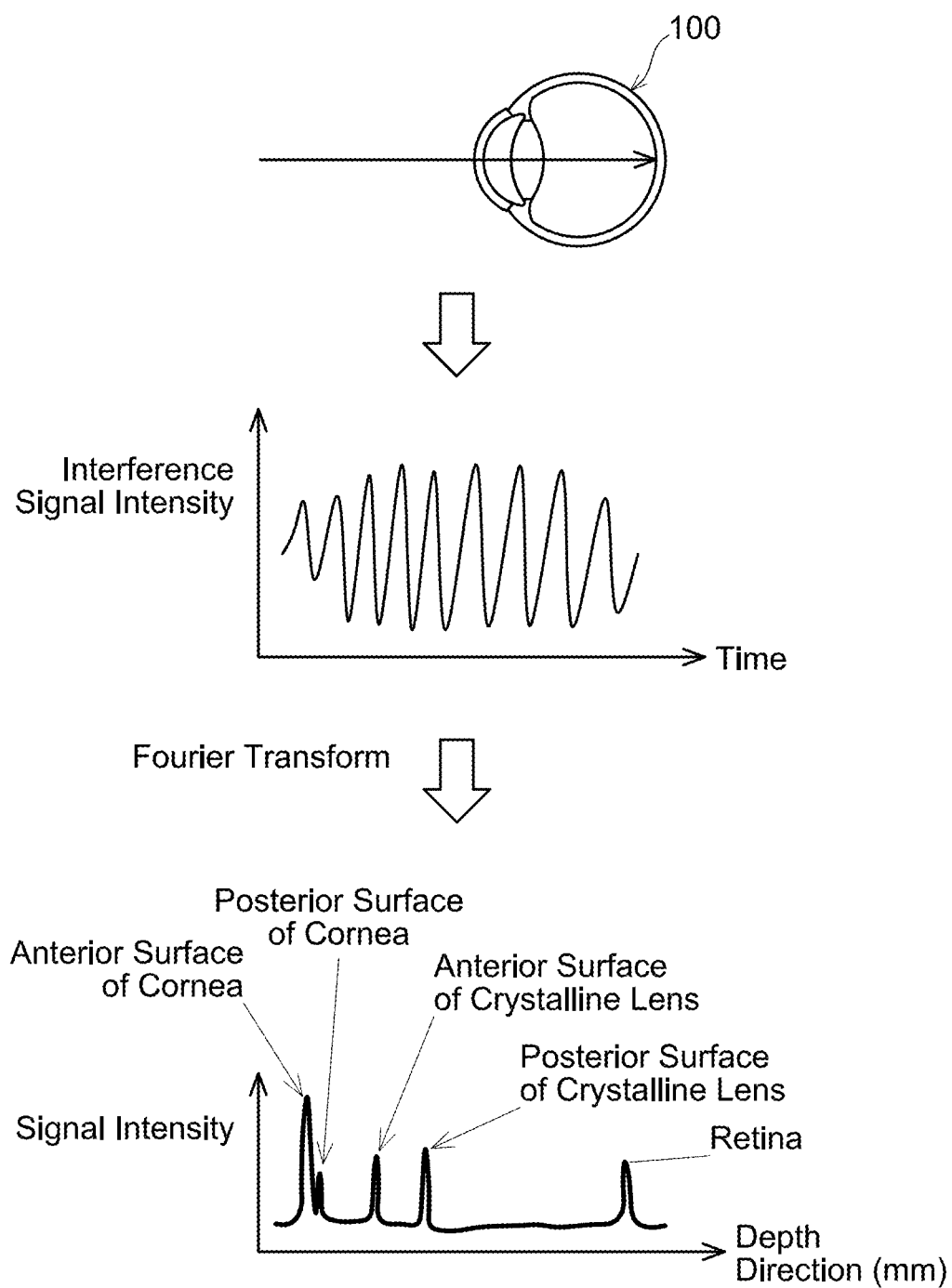
FIG. 4 shows diagrams for explaining a procedure to process an interference signal waveform.

When the adjustment of the Galvano mirror 22 is completed, the processor 60 turns on the light source 12, and acquires the interference signals that were detected by the balance detector 38 and sampled by the AD converter 40 while changing the frequency of the light outputted from the light source 12 (S16). Each of the interference signals outputted from the AD converter 40 is a signal of which signal intensity changes over time as shown in FIG. 4, and this signal is a signal composed of an interference wave that is obtained by combining the reference light and the reflected light reflected at each part of the subject eye E (such as anterior and posterior surfaces of the cornea, anterior and posterior surfaces of the crystalline lens, and the retina). Then, by subjecting the signals inputted from the AD converter 40 to Fourier transform, the processor 60 can extract interference signal components of the reflected light reflected at each part of the subject eye E (such as at the anterior and posterior surfaces of the cornea, the anterior and posterior surfaces of the crystalline lens, and the retina) from these signals. By doing so, the processor 60 can specify positions of the parts of the subject eye E in the depth direction. In the disclosure herein, the acquisition of the interference signals including positional information of the respective parts of the subject eye E in the depth direction by changing the frequency of the light outputted from the light source 12 is termed A-scan.

Next, the processor 60 determines whether or not the measurement of step S16 has been executed for all of scan angles that were set in advance prior to the measurement (that is, for all of the incident positions and the incident angles) (S18). In a case where the measurement of step S16 has not been executed for all the scan angles (NO in step S18), the processor 60 returns to step S14, and the processes from step S14 are repeated. Due to this, the interference signals obtained by the A-scan for each scan angle for scanning the Galvano mirror 22 are thereby acquired. Causing the incident position and the incident angle of the light from the light source 12 to change by changing the scan angle of the Galvano mirror 22 is herein termed a B-scan.

Figure 5:
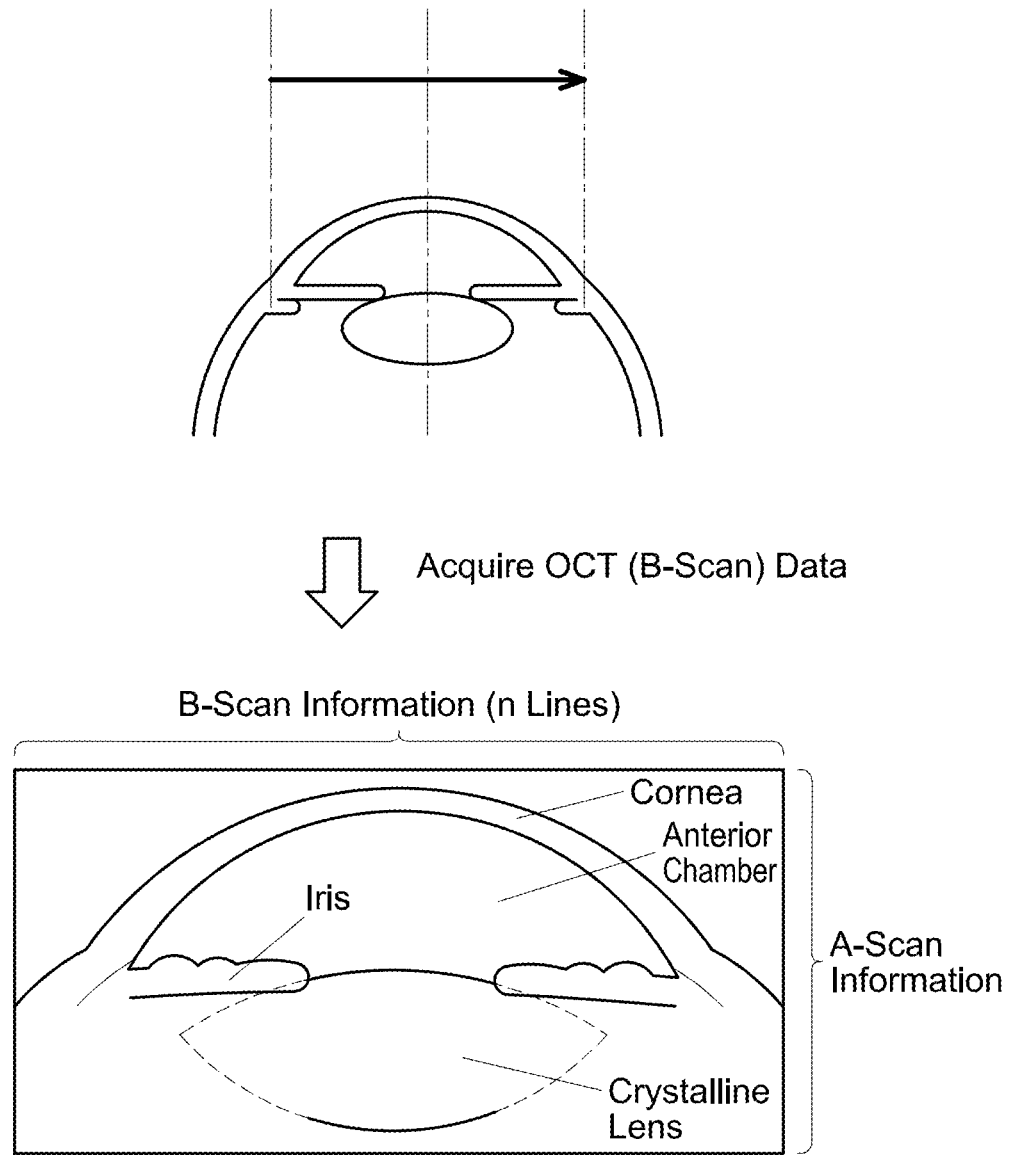
FIG. 5 shows diagrams for explaining a procedure to scan incident positions of light to the subject eye within a predetermined range and to specify a position of each part in the subject eye from information acquired for each incident position (information acquired by the procedure shown in FIG. 4).

On the other hand, in a case where the measurement of step S16 has been executed for all the scan angles (YES in step S18), the processor 60 identifies the positions of the respective parts of the subject eye E (such as the anterior and posterior surfaces of the cornea, the anterior and posterior surfaces of the crystalline lens and the retina) from the interference signals acquired for the respective scan angles (S20). Specifically, when the process of step S16 is executed for each of the scan angles, information on the interference signals (A-scan information) is acquired for each of those scan angles. Accordingly, as shown in FIG. 5, two-dimensional information in which the interference signal information (the A-scan information) are arranged by a number of the scan angles (n lines) is acquired. Due to this, the processor 60 identifies the positions of the respective parts of the subject eye E by calculating borderlines between the respective parts of the subject eye E (such as the cornea, the anterior chamber, an iris, and the crystalline lens) included in the respective interference signal information. The processor 60 writes acquired (captured) tomographic image data in the memory.

Next, the processor 60 determines whether or not the tomographic image data acquired in the aforementioned steps S14 to S20 has been acquired for all of time slots (timepoints of image capturing) that were preset before the measurement (S22). In the present embodiment, a plurality of tomographic images is acquired for a same cross section of the subject eye E in time series. That is, the processor 60 acquires B-scan information for the same cross section of the subject eye E with a preset time interval and with a preset number of times (that is, at all of the timepoints of image capturing within a preset image capturing period). In a case where tomographic images have not been acquired for all of the time slots (NO in step S22), the processor 60 returns to step S14, and the processes from step S14 are repeated. Due to this, the plurality of tomographic image data which have been acquired (captured) is written in the memory in a time series order. On the other hand, in a case where tomographic images have been acquired for all of the time slots (YES in step S22), the processor 60 proceeds to the subsequent process.

Next, an entropy of the generated interference signals is calculated from the acquired plurality of tomographic images (S24). The memory stores the plurality of tomographic image data for the same cross section of the subject eye E by the aforementioned processes up to step S22. Since the plurality of tomographic images is for the same cross section, a difference is less likely to occur among the plurality of images at a stationary part in the scattering sample. That is, the entropy at that part is low. On the other hand, a difference occurs more likely among the plurality of images at a dynamic part in the scattering sample. That is, the entropy at that part is high. Due to this, the dynamic part in the tomographic images can be specified noninvasively and with high accuracy by calculating the entropy from the plurality of images acquired in time series. Further, in a conventional method of specifying a dynamic part from tomographic images, a measurement time for measuring a target region had to be long in order to specify whether a difference among the images captured in time series is caused due to being a dynamic part or due to noise. In the present embodiment, the dynamic part is specified by calculating the entropy, and thus a measurement time for measuring the target region can be made short. The dynamic part in the tomographic images may, for example, be a blood vessel in the subject eye E.

A process of step S24 is executed by a procedure as follows. A complex signal of the interference light acquired at a time t is defined as g(t). In this case, a pair of complex signals of the interference light acquired at the time t and a time t+Δt is defined as in Math 1 as below. E(t) indicates an authentic complex signal (a complex signal that does not include noise component) at the time t, and γ indicates an additive complex white noise.

$$\underline{\chi}(t, t+\Delta t) = \begin{bmatrix} g(t) \\ g(t+\Delta t) \end{bmatrix} = \begin{bmatrix} E(t)+\gamma \\ E(t+\Delta t)+\gamma \end{bmatrix} \quad \text{[Math 1]}$$

The processor 60 calculates an ensemble average of the covariance matrix of above Math 1. The ensemble average of the covariance matrix of Math 1 is represented as in Math 2 below. Each overline indicates an ensemble average, the superscript dagger indicates Hermitian transpose, and each superscript asterisk indicates a complex conjugate.

$$T = \overline{\underline{\chi} \cdot \underline{\chi}^\dagger} = \begin{bmatrix} \overline{|g(t)|^2} & \overline{g(t)g^*(t+\Delta t)} \\ \overline{g(t+\Delta t)g^*(t)} & \overline{|g(t+\Delta t)|^2} \end{bmatrix} \quad \text{[Math 2]}$$

By using an arbitrary integer n, a pair of complex signals of the interference light acquired at a time t+nΔt and a time t+(n+1)Δt may be represented as in Math 3 below.

$$\chi(t+n\Delta t, t+(n+1)\Delta t) \quad \text{[Math 3]}$$

The processor 60 may replace above Math 1 with Math 3 and calculate the ensemble average of the covariance matrix of Math 3. Further, although above Math 2 represents the ensemble average of the covariance matrix at one point in a space, multiple points in a spatially-defined kernel size may be included in the ensemble average.

Next, the processor 60 subjects above Math 2 to eigenvalue decomposition. By so doing, Math 4 below is obtained. Here, $\lambda_1$ and $\lambda_2$ each indicate eigenvalues, where $\lambda_1 \geq \lambda_2 \geq 0$ is satisfied. Further, U indicates a matrix constituted of eigenvectors.

$$T = U \begin{bmatrix} \lambda_1 & 0 \\ 0 & \lambda_2 \end{bmatrix} U^\dagger \quad \text{[Math 4]}$$

Here, $\lambda_1$ and $\lambda_2$ are normalized as shown in Math 5 below.

$$\lambda_i' = \frac{\lambda_i}{\Sigma_j^2 \lambda_j}, i = 1, 2 \quad \text{[Math 5]}$$

When above Math 5 is used, the entropy of the generated interference signals is defined as in Math 6 below. Here, H indicates the entropy of the generated interference signals.

$$H = \sum_i^2 -\lambda_i' \log_2 \lambda_i' \quad \text{[Math 6]}$$

As above, the processor 60 can calculate the entropy of the generated interference signals by using the plurality of tomographic image data for the same cross section of the subject eye E.

In above Math 2, in a case where a number of samples to be used for the ensemble average is insufficient, the processor 60 may correct the eigenvalues of Math 5 as in Math 7 below.

$$\hat{\lambda}_i = \lambda_i - \frac{\lambda_i}{n} \sum_{j=1, j \neq i}^2 \frac{\lambda_j}{\lambda_i - \lambda_j}, i = 1, 2 \quad \text{[Math 7]}$$

In a case of using Math 7 for the eigenvalues instead of above Math 5, the entropy of the generated interference signals is defined as in Math 8 below instead of Math 6.

$$\hat{H} = \sum_i^2 -\hat{\lambda}_i' \log_2 \hat{\lambda}_i', \hat{\lambda}_i' = \frac{\lambda_i}{\Sigma_j^2 \lambda_j} \quad \text{[Math 8]}$$

Thus, the processor 60 may use either one of Math 6 and Math 8 as the entropy of the generated interference signals. Hereinbelow, Math 6 will be used as the entropy of the generated interference signals to facilitate explanation.

When the entropy of the generated interference signals has been calculated, the processor 60 calculates an entropy of noise component in the interference signals (S26). The entropy of the generated interference signals calculated in step S24 includes not only randomness which authentic interference signals have (hereinbelow termed an entropy of the authentic interference signals) but also randomness caused by the noise component (hereinbelow termed an entropy of the noise component). The entropy of the authentic interference signals and the entropy of the noise component are statistically not correlated with each other. Due to this, a sum of the entropy of the authentic interference signals and the entropy of the noise component matches the entropy of the generated interference signals. Therefore, in step S26, the entropy of the noise component is calculated to calculate the entropy of the authentic interference signals.

A process of step S26 is executed by a procedure as follows. Aside from step S24 as above, tomographic images that measured only noise without setting a measurement target in the device are prepared and used for the process of step S26. The equation represented in above Math 1 is a vector with two rows and 1 column, similarly to a Jones vector. Further, Jones vector can be transformed to DOP (degree of polarization). Due to this, the equation represented in Math 1 can be transformed by applying a calculation method for transforming Jones vector to DOP. Then, the processor 60 transforms Math 1 to Math 9 below by using the calculation method for transforming Jones vector to DOP.

$$P = \frac{\sqrt{\left(\overline{|g(t)|^2} - \overline{|g(t+\Delta t)|^2}\right)^2 + 4\left(\overline{|g(t)|^2} - |\gamma|^2\right)\left(\overline{|g(t+\Delta t)|^2} - |\gamma|^2\right)}}{\overline{|g(t)|^2} + \overline{|g(t+\Delta t)|^2}} \quad \text{[Math 9]}$$

Further, DOP transformed from the Jones vectors can further be transformed to eigenvalues. Then, the processor 60 transforms above Math 9 to Math 10 below by using a calculation method for transforming DOP, which has been transformed from Jones vector, to eigenvalues.

$$\zeta_1 = \frac{1+P}{2}, \zeta_2 = \frac{1-P}{2} \quad \text{[Math 10]}$$

By using above Math 10, the entropy of the noise component can be calculated as in Math 11 below. $H_{noise}$ indicates the entropy of the noise component.

$$H_{noise} = \sum_{i=1}^{2} -\zeta_i \log_2 \zeta_i \quad \text{[Math 11]}$$

Next, the processor 60 calculates the entropy of the authentic interference signals (S28). The entropy of the authentic interference signals can be calculated by subtracting the entropy of the noise component from the entropy of the generated interference signals. Thus, an equation represented in Math 12 below is established. Here. $H_{subject}$ indicates the entropy of the authentic interference signals.

$$H_{subject} = H - H_{noise} \quad \text{[Math 12]}$$

The processor 60 assigns the entropy of the interference signals calculated in step S24 and the entropy of the noise component calculated in step S26 to Math 12 to calculate the entropy of the authentic interference signals. In the present embodiment, the entropy of the generated interference signals and the entropy of the noise component are calculated independently from each other. Due to this, even if the interference signals are small, for example, the entropy of the generated interference signals and the entropy of the noise component can be calculated with high accuracy. Thus, the entropy of the authentic interference signals can more accurately be calculated.

Figure 6:
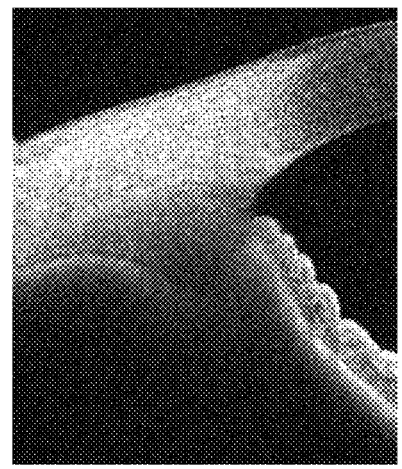
FIG. 6 is a tomographic image in a vicinity of a corner angle of the subject eye, and is an image indicating a signal intensity.
Figure 7A:
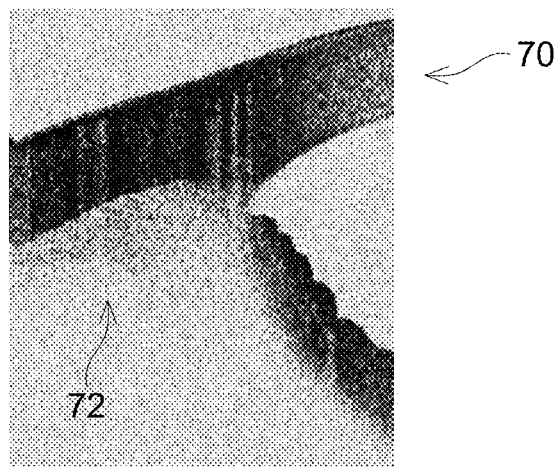
FIGS. 7A to 7C are images indicating entropies at a part matching that of the tomographic image of FIG. 6, where 7A is an image indicating an entropy of generated interference signals, 7B is an image indicating an entropy of noise component, and 7C is an image acquired by subtracting the entropy of the noise component from the entropy of the generated interference signals.
Figure 7B:
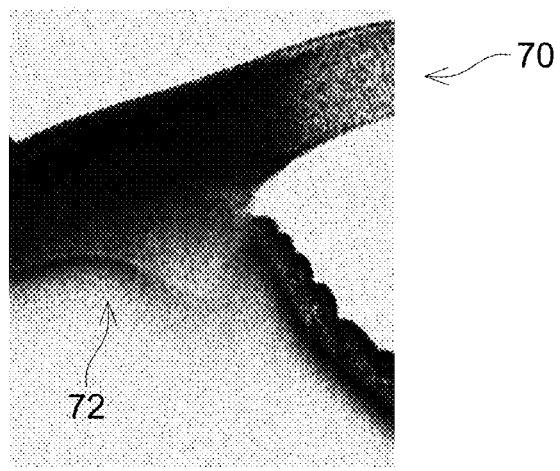
Figure 7C:
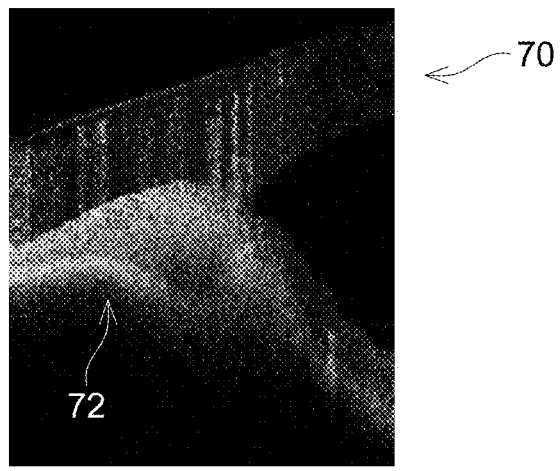

In an experiment conducted by the inventor of the present disclosure, it has been confirmed that the entropy of the authentic interference signals can be calculated accurately by subtracting the entropy of the noise component from the entropy of the generated interference signals. FIGS. 6 and 7A to 7C show tomographic images near the corner angle of the subject eye E. FIG. 6 is an image indicating an intensity of the interference signals, and FIGS. 7A to 7C are images respectively indicating entropies at a portion matching that of the image of FIG. 6. More specifically, FIG. 7A is an image indicating the entropy of the generated interference signals, FIG. 7B is an image indicating the entropy of the noise component, and FIG. 7C is an image obtained by subtracting the entropy of the noise component from the entropy of the generated interference signals. A portion in FIGS. 7A to 7C denoted by a reference sign 70 (hereinbelow termed a portion 70) indicates a part of the cornea, and a portion denoted by a reference sign 72 (hereinbelow termed a portion 72) indicates a part of a ciliary body. In FIGS. 7A to 7C, portions with high entropy are shown in white and portions with low entropy are shown in black.

The entropy is low in the portion 70 since no blood vessel is present in the cornea, and the entropy is high in the portion 72 since the ciliary body includes a large number of blood vessels. As shown in FIG. 7A, the entropy of the generated interference signals is extremely high in the portion 72 indicating the ciliary body, however, it is also relatively high in the portion 70 indicating the cornea as well, though it is somewhat lower than that of the portion 72 indicating the ciliary body.

Contrary to this, as shown in FIG. 7B, the entropy of the noise component is high in the portion 70 indicating the cornea. Accordingly, the entropy of the generated interference signals in the portion 70 indicating the cornea (see FIG. 7A) can be said as being high due to the noise component. Further, the entropy of the noise component is somewhat high also in the portion 72 indicating the ciliary body. Due to this, the entropy of the generated interference signals in the portion 72 indicating the ciliary body (see FIG. 7A) can also be said as including the noise component to some degree.

As shown in FIG. 7C, when the entropy of the noise component was subtracted from the entropy of the generated interference signals, the entropy of the interference signals became low in the portion 70 indicating the cornea. That is, it has been indicated that no blood vessel is present in the portion 70 indicating the cornea. Further, the entropy of the interference signals was sufficiently high in the portion 72 indicating the ciliary body. That is, it has been indicated that the large number of blood vessels are present in the portion 72 indicating the ciliary body. Thus, it has been confirmed that the entropy of the interference signals can accurately be calculated by subtracting the entropy of the noise component from the entropy of the generated interference signals.

Next, the processor 60 specifies a dynamic part of the subject eye E from the calculated entropy of the authentic interference signals (S30). Specifically, the processor 60 specifies a portion with high entropy of the authentic interference signals calculated in step S28 as the dynamic part of the subject eye E. When the dynamic part is specified, the processor 60 writes data of the image indicating the entropy of the authentic interference signals in the memory, and terminates the process of specifying the dynamic part of the subject eye E.

Figure 8A:
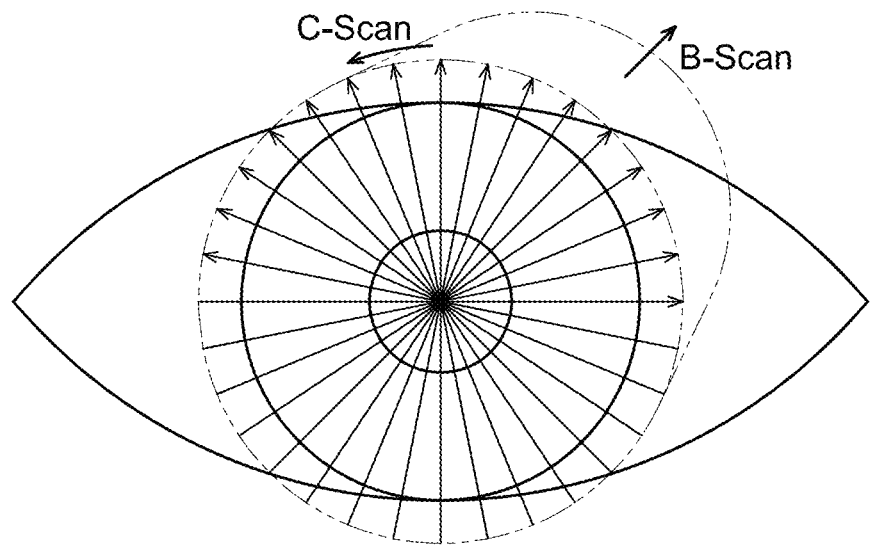
FIGS. 8A and 8B are diagrams for explaining a radial scan scheme.
Figure 8B:
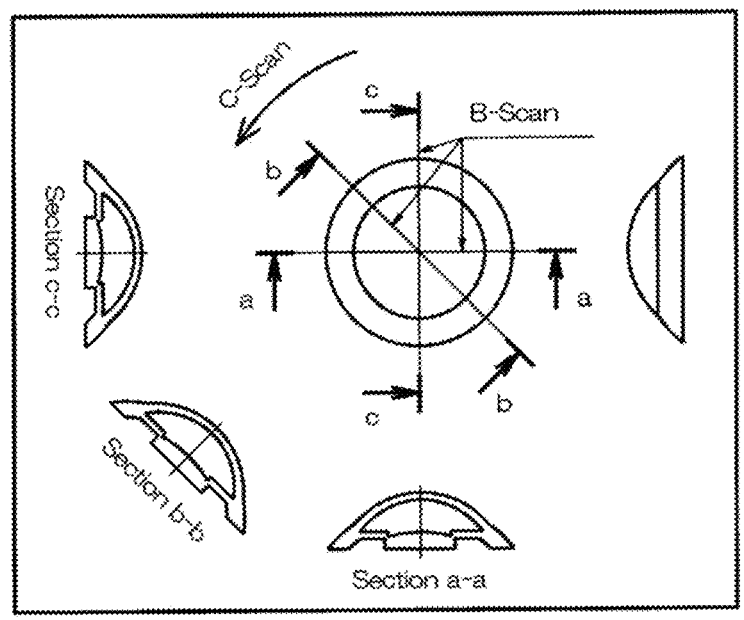

In the present embodiment, the dynamic part is specified in the tomographic images of the single cross section, however, no limitation is placed to this configuration. For example, the dynamic part specifying process as above may be executed while the position of a cross section of the subject eye E is changed, and three-dimensional data may be acquired from tomographic images for a plurality of cross sections. For example, as shown in FIGS. 8A and 8B, the tomographic images for the plurality of cross sections may be acquired by a radial scan scheme in which each scan line passes through an apex of the cornea. In so doing, the plurality tomographic images is captured for each cross section in time series. By so doing, the plurality of tomographic images of the subject eye E is acquired in time series for all of the cross sections. That is, the tomographic images are acquired with a B-scan direction set in radial directions from the apex of the cornea of the subject eye E and a C-scan direction set in a circumferential direction thereof. Further, the processor 60 calculates the entropy of the authentic interference signals and specifies the dynamic part for the tomographic images of each cross section that were acquired, to construct three-dimensional data. Due to this, the three-dimensional data of the dynamic part of the subject eye E can be acquired. A method of acquiring the three-dimensional data is not particularly limited. For example, the tomographic images for the plurality of cross sections may be acquired by a raster scan scheme.

Further, a front image of the subject eye E may be acquired by using the three-dimensional data of the entropy constructed as above (hereinbelow may be termed three-dimensional entropy data). The front image is, for example, an en face image. Specifically, a maximum value, an average value and the like in the depth direction are calculated for each A-scan in the three-dimensional entropy data, and the three-dimensional data is compressed into a two-dimensional en face image. By showing the dynamic part in the two-dimensional en face image, the examiner can more easily grasp the dynamic part of the target object.

Moreover, three-dimensional data may be acquired plural times for a same part in the subject eye E (such as the anterior part), and a maximum value and an average value at each position in a plurality of three-dimensional entropy data or at each position in a plurality of the two-dimensional entropy en face images may be calculated. Due to this, measurement noise can be reduced. Further, the data acquired plural times may not indicate exactly the same position, due to motions of the subject eye E. Thus, the measurement noise can more efficiently be reduced by carrying out accurate positioning for the part that was captured plural times prior to the calculation of the maximum value and the average value of the entropy at each position.

Further, in the present embodiment, the blood vessel in the subject eye E is specified, however, no limitation is placed to this configuration. Any dynamic part in the scattering sample can be specified by calculating the entropy from the plurality of tomographic images for the same cross section, and for example, not only the blood vessel in the anterior part of the eye, but also a blood vessel in the fundus, a cerebral vessel, and a hypodermic blood vessel can be specified.

Further, the optical coherence tomographic device according to the present embodiment specifies the dynamic part of the scattering sample by using OCT, however, a type of OCT is not particularly limited. For example, the optical coherence tomographic device may be a polarization-sensitive optical coherence tomographic device.

Specific examples of the disclosure herein have been described in detail, however, these are mere exemplary indications and thus do not limit the scope of the claims. The art described in the claims includes modifications and variations of the specific examples presented above. Technical features described in the description and the drawings may technically be useful alone or in various combinations, and are not limited to the combinations as originally claimed.

What is claimed is:

1. An optical coherence tomographic device comprising:
   a light source;
   a measurement light generator configured to generate measurement light by using light from the light source and to generate reflected light from a target region in a scattering sample by irradiating the target region with the measurement light;
   a reference light generator configured to generate reference light by using the light from the light source:
   an interference light generator configured to generate interference light by combining the reflected light from the target region generated in the measurement light generator and the reference light generated in the reference light generator;
   an interference light detector configured to detect the interference light generated in the interference light generator and to generate interference signals by converting the interference light;
   a processor; and
   a memory storing computer-readable instructions therein, the computer-readable instructions, when executed by the processor, causing the optical coherence tomographic device to execute:
   acquiring a plurality of tomographic images for a same cross section in the target region in time series from the interference signals generated in the interference light detector:
   calculating an entropy of the generated interference signals based on the plurality of tomographic images acquired in time series; and
   specifying a dynamic part in the tomographic images based on the calculated entropy of the generated interference signals.

2. The optical coherence tomographic device according to claim 1, wherein
   the computer-readable instructions, when executed by the processor, further cause the optical coherence tomographic device to execute:
   calculating an entropy of noise component in the generated interference signals based on the plurality of tomographic images acquired in time series; and
   correcting the entropy of the generated interference signals by subtracting the entropy of noise component from the entropy of the generated interference signals.

3. The optical coherence tomographic device according to claim 1, wherein
   the computer-readable instructions, when executed by the processor, further cause the optical coherence tomographic device to execute:
   acquiring a plurality of tomographic images for each of a plurality of cross sections in the target region in time series; and
   generating specified tomographic images respectively for the plurality of cross sections by executing the calculating of the entropy of the generated interference signals and the specifying of the dynamic part to each of the plurality of cross sections, each of the specified tomographic images specifying the dynamic part in corresponding one of the plurality of cross sections.

4. The optical coherence tomographic device according to claim 3, wherein
   the computer-readable instructions, when executed by the processor, further cause the optical coherence tomographic device to execute:
   generating a front image of the target region by using three-dimensional image data obtained by superimposing the specified tomographic images.

5. The optical coherence tomographic device according to claim 2, wherein
   the computer-readable instructions, when executed by the processor, further cause the optical coherence tomographic device to execute:
   acquiring a plurality of tomographic images for each of a plurality of cross sections in the target region in time series; and
   generating specified tomographic images respectively for the plurality of cross sections by executing the calculating of the entropy of the generated interference signals and the specifying of the dynamic part to each of the plurality of cross sections, each of the specified tomographic images specifying the dynamic part in corresponding one of the plurality of cross sections.

6. The optical coherence tomographic device according to claim 5, wherein
the computer-readable instructions, when executed by the processor, further cause the optical coherence tomographic device to execute:
generating a front image of the target region by using three-dimensional image data obtained by superimposing the specified tomographic images.

7. The optical coherence tomographic device according to claim 1, wherein
the target region comprises a blood vessel, and
the dynamic part is the blood vessel.

* * * * *